(12) United States Patent
Kazala, Jr. et al.

(10) Patent No.: US 9,011,393 B2
(45) Date of Patent: Apr. 21, 2015

(54) SYSTEMS, METHODS, AND DEVICES FOR RESTORING LYMPHATIC FLOW ASSOCIATED WITH A SUBCUTANEOUS DEFECT IN A PATIENTS BODY

(75) Inventors: Richard Marvin Kazala, Jr., San Antonio, TX (US); Eric Woodson Barta, San Antonio, TX (US); Luis Toro, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 193 days.

(21) Appl. No.: 12/904,649

(22) Filed: Oct. 14, 2010

(65) Prior Publication Data
US 2011/0152796 A1   Jun. 23, 2011

Related U.S. Application Data

(60) Provisional application No. 61/287,950, filed on Dec. 18, 2009.

(51) Int. Cl.
*A61M 1/00* (2006.01)
*B23P 17/04* (2006.01)

(52) U.S. Cl.
CPC .................................. *A61M 1/0088* (2013.01)

(58) Field of Classification Search
USPC ......... 604/289–290, 304, 313, 315, 317–327, 604/540–543; 29/428; D24/127
See application file for complete search history.

(56) References Cited

U.S. PATENT DOCUMENTS

| | | | |
|---|---|---|---|
| 1,355,846 | A | 10/1920 | Rannells |
| 2,547,758 | A | 4/1951 | Keeling |
| 2,632,443 | A | 3/1953 | Lesher |
| 2,682,873 | A | 7/1954 | Evans et al. |

(Continued)

FOREIGN PATENT DOCUMENTS

| | | |
|---|---|---|
| AU | 550575 A1 | 8/1982 |
| AU | 745271 | 4/1999 |

(Continued)

OTHER PUBLICATIONS

N. A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96.

(Continued)

*Primary Examiner* — Nicholas Lucchesi
*Assistant Examiner* — Andrew S Lo (57) ABSTRACT

Methods, devices, and systems are disclosed that help to restore lymphatic flow associated with a subcutaneous defect in a patient's body by approximating portions of the subcutaneous defect using reduced pressure and a tissue-approximating device. The tissue approximating device may include a curved member that is formed from a semi-rigid material and defines a concave space that goes over the subcutaneous defect. A flange portion is formed on the curved member. A reduced-pressure aperture is formed on the curved member for providing reduced pressure to the concave space. The tissue-approximating device also includes a spacer member disposed on a tissue-facing side of the curved member and aligned substantially with the reduced-pressure aperture. Other systems, devices, and methods are disclosed.

32 Claims, 5 Drawing Sheets

(56) References Cited

U.S. PATENT DOCUMENTS

| | | |
|---|---|---|
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,192,070 A | 3/1993 | Nagai et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,370,610 A | 12/1994 | Reynolds |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 5,701,917 A | 12/1997 | Khouri |
| 5,803,926 A | 9/1998 | Neward |
| 5,865,827 A | 2/1999 | Bullister |
| 5,935,136 A | 8/1999 | Hulse et al. |
| 5,941,859 A * | 8/1999 | Lerman ................ 604/289 |
| 6,071,267 A | 6/2000 | Zamierowski |
| 6,135,116 A | 10/2000 | Vogel et al. |
| 6,174,306 B1 | 1/2001 | Fleischmann |
| 6,241,747 B1 | 6/2001 | Ruff |
| 6,287,316 B1 | 9/2001 | Agarwal et al. |
| 6,345,623 B1 | 2/2002 | Heaton et al. |
| 6,375,240 B1 | 4/2002 | Lindberg |
| 6,488,643 B1 | 12/2002 | Tumey et al. |
| 6,493,568 B1 | 12/2002 | Bell et al. |
| 6,500,112 B1 | 12/2002 | Khouri |
| 6,553,998 B2 | 4/2003 | Heaton et al. |
| 6,752,794 B2 | 6/2004 | Lockwood et al. |
| 6,814,079 B2 | 11/2004 | Heaton et al. |
| 6,979,324 B2 | 12/2005 | Bybordi et al. |
| 8,034,038 B2 * | 10/2011 | Biggie et al. ............... 604/319 |
| 2001/0043943 A1 | 11/2001 | Coffey |
| 2002/0077661 A1 | 6/2002 | Saadat |
| 2002/0111591 A1 * | 8/2002 | McKinnon et al. ......... 604/289 |
| 2002/0115951 A1 | 8/2002 | Norstrem et al. |
| 2002/0120185 A1 | 8/2002 | Johnson |
| 2002/0143286 A1 | 10/2002 | Tumey |
| 2005/0261642 A1 * | 11/2005 | Weston ..................... 604/313 |
| 2005/0261643 A1 * | 11/2005 | Bybordi et al. ............. 604/313 |
| 2007/0265585 A1 * | 11/2007 | Joshi et al. ................. 604/313 |
| 2008/0300578 A1 * | 12/2008 | Freedman .................. 604/543 |
| 2008/0306456 A1 * | 12/2008 | Riesinger .................. 604/316 |
| 2009/0227969 A1 * | 9/2009 | Jaeb et al. .................. 604/313 |
| 2009/0299303 A1 * | 12/2009 | Seegert ..................... 604/290 |
| 2009/0299307 A1 * | 12/2009 | Barta et al. ................ 604/319 |
| 2009/0299340 A1 * | 12/2009 | Kazala et al. .............. 604/543 |
| 2009/0299341 A1 * | 12/2009 | Kazala et al. .............. 604/543 |
| 2009/0312728 A1 * | 12/2009 | Randolph et al. .......... 604/319 |
| 2011/0009838 A1 * | 1/2011 | Greener .................... 604/319 |
| 2011/0028918 A1 * | 2/2011 | Hartwell ................... 604/319 |
| 2011/0092927 A1 * | 4/2011 | Wilkes et al. .............. 604/304 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |

(56) References Cited

FOREIGN PATENT DOCUMENTS

| | | |
|---|---|---|
| WO | WO 94/20041 | 9/1994 |
| WO | WO 96/05873 | 2/1996 |
| WO | WO 97/18007 | 5/1997 |
| WO | WO 99/13793 | 3/1999 |

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, Managing Draining Wounds and Fistulae: "New and Established Methods," *Chronic Wound Care*, edited by D. Krasner (Health Management Publications, Inc., King of Prussia, PA 1990), pp. 240-246.

G. Živadinović, V. Đukić, Ž. Maksimović, Đ. Radak, and P. Peška, "Vacuum Therapy in the Treatment of Peripheral Blood Vessels," *Timok Medical Journal* 11 (1986), pp. 161-164.

F.E. Johnson, "An Improved Technique for Skin Graft Placement Using a Suction Drain," *Surgery, Gynecology, and Obstetrics* 159 (1984), pp. 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967).

M. Schein, R. Saadia, J.R. Jamieson, and G.A.G. Decker, "The 'Sandwich Technique' in the Management of the Open Abdomen," *British Journal of Surgery* 73 (1986), pp. 369-370.

D.E. Tribble, An Improved Sump Drain-Irrigation Device of Simple Construction, *Archives of Surgery* 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax," *Journal of the American Medical Association* 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians (Jul. 2007).

\* cited by examiner

SYSTEMS, METHODS, AND DEVICES FOR RESTORING LYMPHATIC FLOW ASSOCIATED WITH A SUBCUTANEOUS DEFECT IN A PATIENTS BODY

RELATED APPLICATION

The present invention claims the benefit, under 35 USC §119(e), of the filing of U.S. Provisional Patent Application Ser. No. 61/287,950, entitled "Systems, Methods, and Devices for Restoring Lymphatic Flow Associated with a Subcutaneous Defect in a Patient's Body," filed Dec. 18, 2009, which is incorporated herein by reference for all purposes.

BACKGROUND

The present disclosure relates generally to medical treatment systems, and more particularly, to systems, methods, and devices for helping to restore lymphatic flow associated with a subcutaneous defect in a patient's body.

Physicians perform millions of surgical procedures each year around the world. Many of the procedures are performed as open surgery and an increasing number are performed using minimally invasive surgery, such as endoscopic, arthroscopic, and laparoscopic procedures. As one example, the American Society for Aesthetic Plastic Surgery reports that there were more than 450,000 liposuction procedures in the United States in 2007.

Surgical procedures involve acute wounds, e.g., an incision, in the skin and related tissue. In many instances, the incision is closed at the conclusion of the procedure using a mechanical apparatus, such as staples or suture, or closed using adhesives. Thereafter, the wound is often merely covered with a dry, sterile bandage. Of course, there is usually more disruption than just at the epidermis.

With many surgical procedures, particularly those done with minimally invasive techniques, much of the disruption or damage is below the epidermis at a subcutaneous level. Again, as one example, in one type of liposuction procedure, after the introduction of a tumescent fluid (saline, mild painkiller, and epinephrine), the surgeon will use a trocar and cannula with suction to remove fatty areas. In doing so, it is not uncommon to have subcutaneous voids and other tissue defects formed at tissue sites remote from the incision through which the cannula was placed or at other incisions through which equipment was placed. The damaged tissue will need time and care to heal and poses a number of potential complications and risks including edema, seroma, hematoma, further bruising, and ecchymosis to name some. Various procedures or injuries may create issues with lymphatic flow in the patient.

SUMMARY

Improvements over existing tissue treatment methods, dressings, and systems may be realized by the illustrative, non-limiting embodiments herein. According to an illustrative, non-limiting embodiment, a method for helping to restore lymphatic flow associated with a subcutaneous defect in a patient's body and which is associated with a surface wound includes the steps of: deploying a tissue-approximating device over the subcutaneous tissue and the surface wound, fluidly coupling a reduced-pressure source to the a concave space of the tissue-approximating device, and causing the reduced-pressure source to deliver reduced pressure to the concave space whereby portions of the subcutaneous tissue are approximated. The tissue-approximating device includes a curved member having an inner perimeter and an outer perimeter and having an apex. The curved member defines a concave space on a tissue-facing side. The tissue-approximating device further includes a flange portion of the curved member between the inner perimeter and outer perimeter. The curved member and flange portion are formed from a semi-rigid material. A reduced-pressure aperture is formed on the curved member for providing reduced pressure to the concave space. The tissue-approximating device also includes a spacer member disposed on the tissue-facing side of the curved member and aligned substantially with the reduced-pressure aperture.

According to another illustrative, non-limiting embodiment, a tissue-approximating device for approximating subcutaneous tissue to help restore lymphatic flow includes a curved member having an inner perimeter and an outer perimeter and having an apex. The curved member defines a concave space on a tissue-facing side. The tissue-approximating device further includes a flange portion of the curved member between the inner perimeter and outer perimeter. The curved member and flange portion are formed from a semi-rigid material. A reduced-pressure aperture is formed on the curved member for providing reduced pressure to the concave space. The tissue-approximating device also includes a spacer member disposed on the tissue-facing side of the curved member and aligned substantially with the reduced-pressure aperture.

According to another illustrative, non-limiting embodiment, a method of manufacturing a tissue-approximating device for helping to restore lymphatic flow associated with a subcutaneous defect in a patient's body includes forming a curved member having an inner perimeter and an outer perimeter and having an apex. The curved member defines a concave space on a tissue-facing side. The method further includes forming a flange portion of the curved member between the inner perimeter and outer perimeter, forming a reduced-pressure aperture formed on the curved member for providing reduced pressure to the concave space, and providing a spacer member for placement proximate to the tissue-facing side of the curved member. The curved member and flange portion are formed from a semi-rigid material.

Other features and advantages of the illustrative embodiments will become apparent with reference to the drawings and detailed description that follow.

DETAILED DESCRIPTION

In the following detailed description of the non-limiting, illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
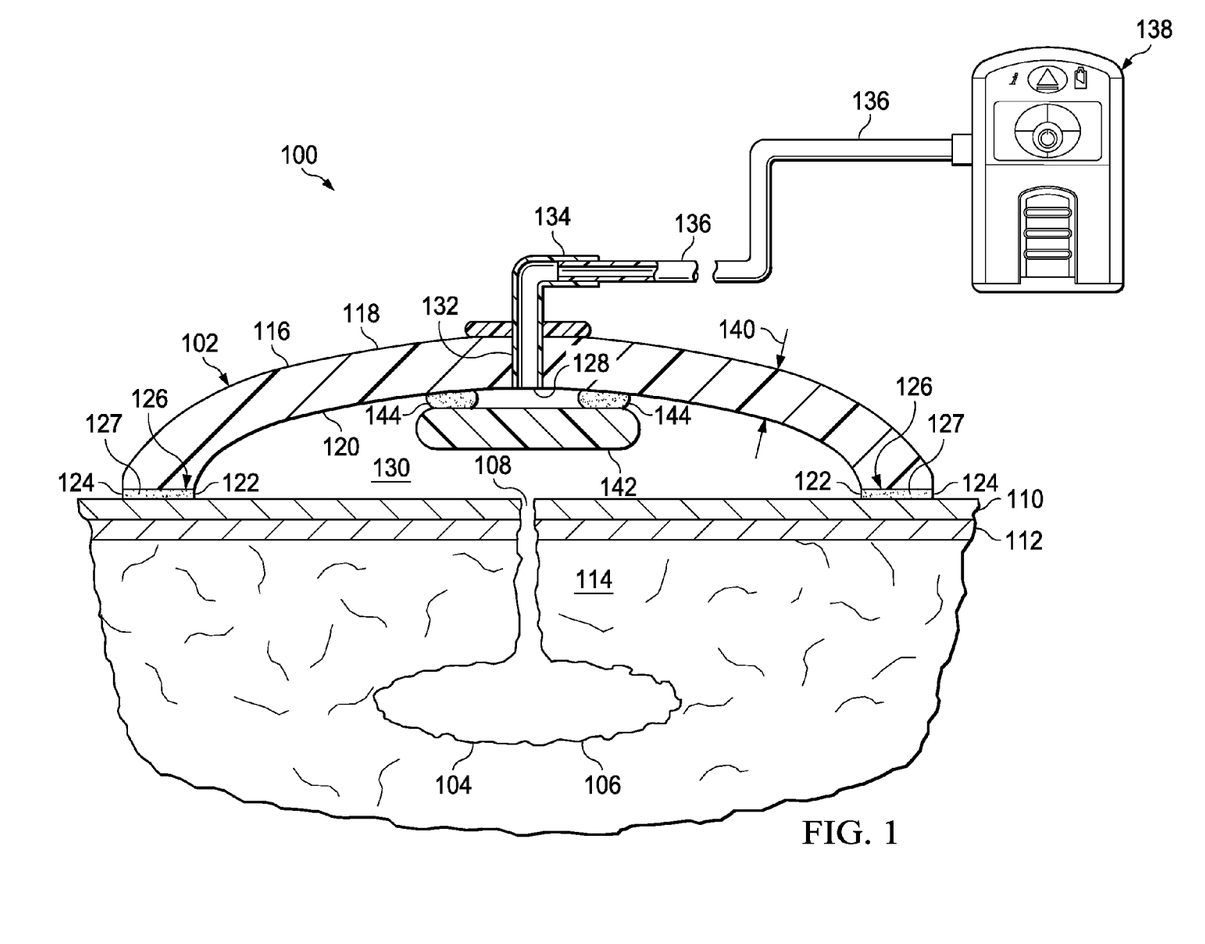
FIG. 1 is a schematic diagram with a portion in cross section of an illustrative, non-limiting embodiment of a system for helping to restore lymphatic flow associated with a subcutaneous defect in a patient's body.
Figure 2:
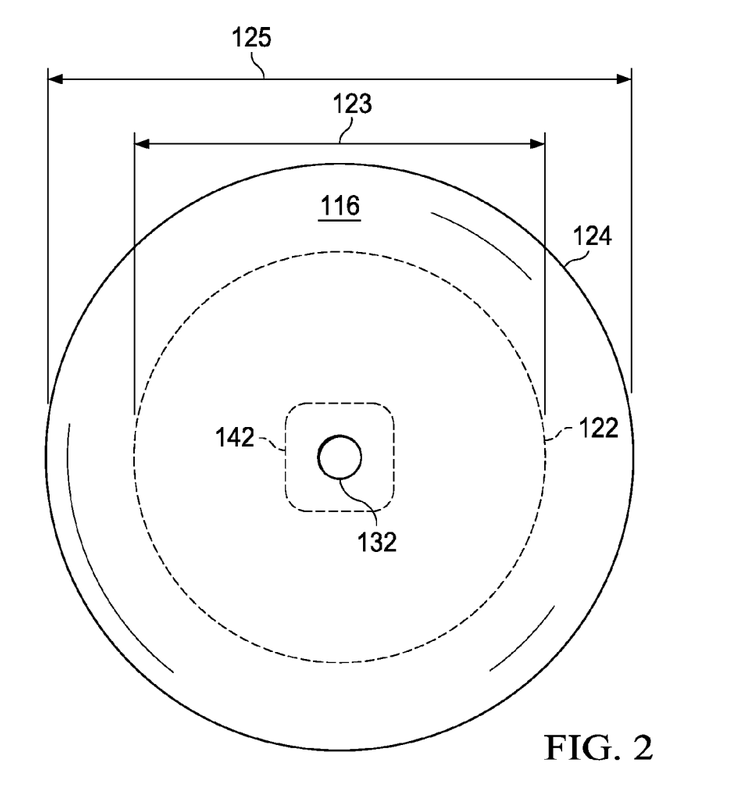
FIG. 2 is a plan view of a portion of the system of FIG. 1 showing a curved member.
Figure 3:
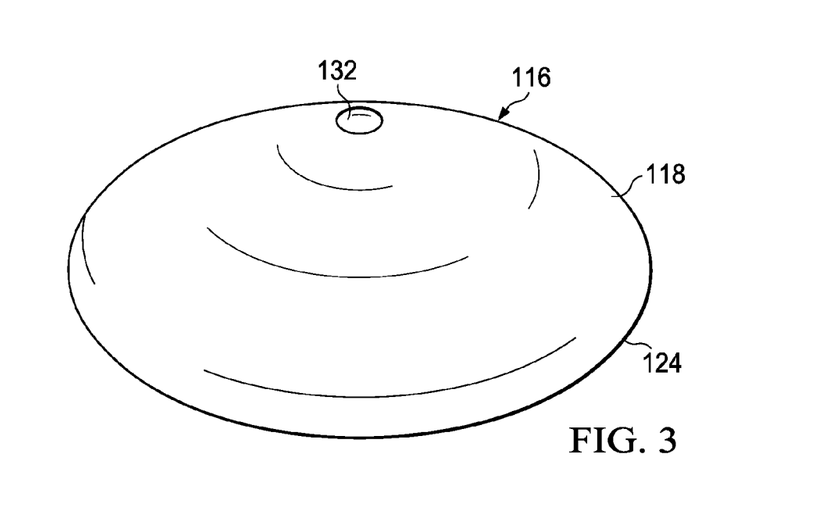
FIG. 3 is a perspective view of the curved member of FIG. 2.
Figure 4:
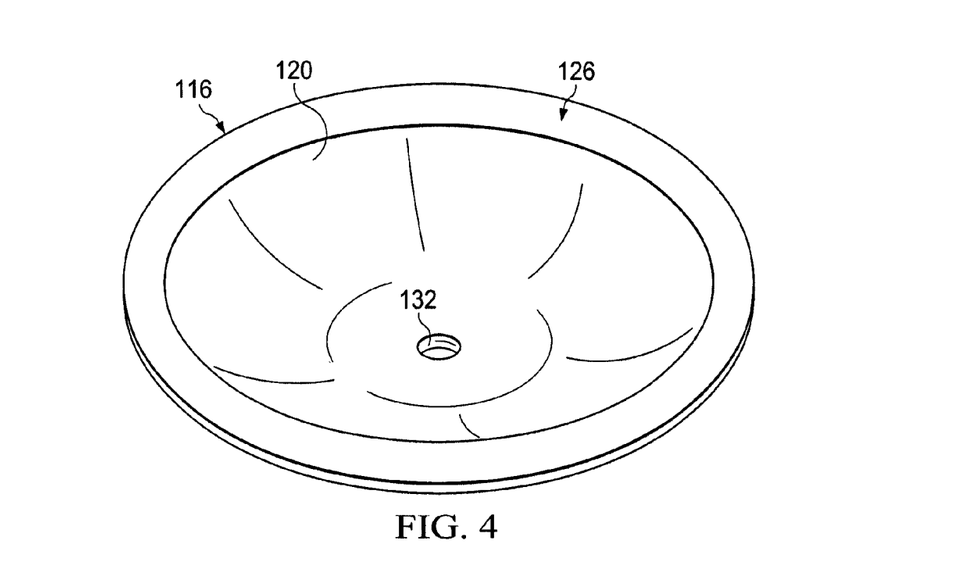
FIG. 4 is another perspective view of the curved member of FIGS. 2 and 3.

Referring to FIGS. 1-5 and initially to FIG. 1, a tissue-approximating system 100 with a tissue-approximating device 102 is presented. The tissue-approximating device 102 is shown deployed over a subcutaneous defect 104, such as a void 106. The tissue-approximating device 102 is also over a surface wound 108 that may be associated with the subcutaneous defect 104 and that is adjacent to epidermis tissue 110. The surface wound 108 may extend through the epidermis 110, dermis 112, and into subcutaneous tissue 114.

The subcutaneous defect 104 may be formed by a surgical procedure, such as liposuction or retraction, from trauma, or in other ways. Without intervention, the subcutaneous defect 104 typically leads to a natural build up of fluids. The subcutaneous defect 104, at some level, disrupts lymphatic flow, which helps to remove the fluids that may have collected because of the creation of the subcutaneous defect 104. The tissue-approximating device 102 helps close or approximate the subcutaneous defect 104 and to restore lymphatic flow to help remove fluids that otherwise would remain longer. The restored lymphatic flow should lead to quicker healing times.

The tissue-approximating device 102 includes a curved member 116 that has a first side 118 and a second, tissue-facing side 120. The curved member 116 may be formed with an inner perimeter 122 and an outer perimeter 124 that define a flange portion 126. The inner perimeter 122 defines a first diameter 123 and the outer perimeter 124 defines a second diameter 125. The curved member 116 has an apex 128, which in the cross section of FIG. 1 is the most vertical (for the orientation shown) portion. The apex 128 is displaced from the flange portion 126 in two dimensions. A portion of the curved member 116 defines a concave space 130 inboard of the inner perimeter 122 and including the apex 128 on the second, tissue-facing side 120 of the curved member 116. The concave space 130 may be substantially concave to define an open space. When in use, tissue may be pulled within the concave space 130 and may fully or partially fill the concave space 130.

A sealing device 127 may be added to the flange portion 126 to help seal the curved member 116 against the patient's epidermis 110 to provide a fluid seal or stability. The sealing device 127 may be an adhesive, a hydrocolloid, a hydrogel, a saline ring with adhesive, or other sealing device. The strength or quantity of the sealing device 127 may be adjusted according to the application, e.g., an abdominal wound on which the curved member 116 remains fairly flat will not need as much strength as when applied to a curved body part. An additional sealing device (not shown), e.g., drape, may be added to help form the fluid seal in some situations.

The flange portion 126 may be sized to transmit forces from the curved member 116 to the patient's epidermis 110 with only minimal discomfort to the patient. The curve and tapered shape of the curved member 116 is to facilitate the transmission of tangential forces within the curved member 116 onto the flange portion 126.

A reduced-pressure aperture 132 may formed on the curved member 116 and in this illustrative embodiment is located at the apex 128, but could be anywhere on the curved member 116. The reduced-pressure aperture 132 facilitates fluidly coupling a reduced-pressure interface 134 to the curved member 116 such that reduced pressure may be delivered to the concave space 130. The reduced-pressure interface 134 may be any device for facilitating delivery of reduced pressure to the concave space 130. In one illustrative embodiment, the reduced-pressure interface 134 is a T.R.A.C.® Pad or Sensa T.R.A.C.® Pad available from KCI of San Antonio, Tex. The reduced-pressure interface 134 may have a portion extending through the reduced-pressure aperture 132 or may rest over the aperture and in fluid communication therewith.

A reduced-pressure delivery conduit 136 fluidly couples the reduced-pressure interface 134 to a reduced-pressure source 138. The reduced-pressure source 138 provides reduced pressure. The reduced-pressure source 138 may be any device for supplying a reduced pressure, such as a vacuum pump, wall suction, or other source. While the amount and nature of reduced pressure applied will typically vary according to the application, the reduced pressure will typically be between −80 mm Hg and −400 mm Hg and more typically between −90 mm Hg and −220 mm Hg.

The curved member 116 is formed from a semi-rigid material that is operable to allow the curved member 116 to carry a load when under reduced pressure, but flexible enough to allow some movement and to provide comfort for the wearer. The load may be carried by a tangential loading of the curved member 116, which may be a dome-shaped or bowl-shaped member. For example, the curved member may be formed from a semi-rigid, medical-grade polymer; silicone; polyvinyl chloride, or other semi-rigid material. In one illustrative, non-limiting embodiment, the curved member 116 has a thickness 140(*t*) that is ⅙ to 1/12 of the first diameter 123, but could be other thicknesses as well depending on the strength of the material from which the curved member 116 is formed. The curved member 116 may be formed using any suitable technique, such as molding. In one illustrative, non-limiting embodiment, the curved member 116 is formed by molding silicone. The curved member 116 may be shaped or formed to accommodate different body parts.

A spacer member 142, or spacer, is disposed within the concave space 130. The spacer member 142 may be positioned between the reduced-pressure aperture 132 and the patient's epidermis 110 or elsewhere within the concave space 130. The spacer member 142 functions to prevent the reduced-pressure aperture 132 or a portion of the reduced-pressure interface 134 from becoming sealed by the epidermis 110 under certain conditions. Without the spacer member 142, under sufficient reduced pressure, the epidermis 110 of the patient could be pulled into the concave space 130 to an extent that the reduced-pressure aperture 132 would become sealed or blocked. With the spacer member 142 in place, the spacer will provide a breathable space that inhibits or prevents sealing of the reduced-pressure aperture 132. The spacer member 142 may be any material or device that allows for the reduced-pressure aperture 132 to remain open to fluid flow even as epidermis 110 is pulled into the concave space 130. For example, the spacer may be a material with a plurality of flow channels, a foam, a non-woven material, a felt member, a member with a plurality of rings and cross channels or other material.

The spacer member 142 may be disposed in the concave space 130 in a size that will substantially assure that the spacer member 142 remains between the reduced-pressure aperture 132 and the patient's epidermis 110. The spacer member 142 may be any size larger than the reduced-pressure aperture 132. An attachment device 144 may be added to secure the spacer member 142 in relative position. The attachment device 144 may be a weld (e.g., ultrasonic or RF weld), bond, adhesive, cement or other attachment device or technique.

In operation, the curved member 116 is placed over the subcutaneous defect 104 and over the surface wound 108 as shown in FIG. 1. If not already installed, the reduced-pressure interface 134 is installed onto to the reduced-pressure aperture 132. If not already installed, the reduced-pressure delivery conduit 136 is installed to fluidly couple the reduced-pressure interface 134 and the reduced-pressure source 138.

The reduced-pressure source 138 is activated and reduced pressure is delivered to the concave space 130. The flange portion 126 provides a fluid seal with the patient's epidermis 110. "Fluid seal," or "seal," means a seal adequate to maintain reduced pressure at a desired site given the particular reduced-pressure source or subsystem involved. As the reduced pressure increases in the concave space 130, the epidermis 110 and other tissue may be pulled, at least in part, into the concave space 130. The reduced pressure may be applied with a variable or cyclic pattern or constantly.

Figure 5:
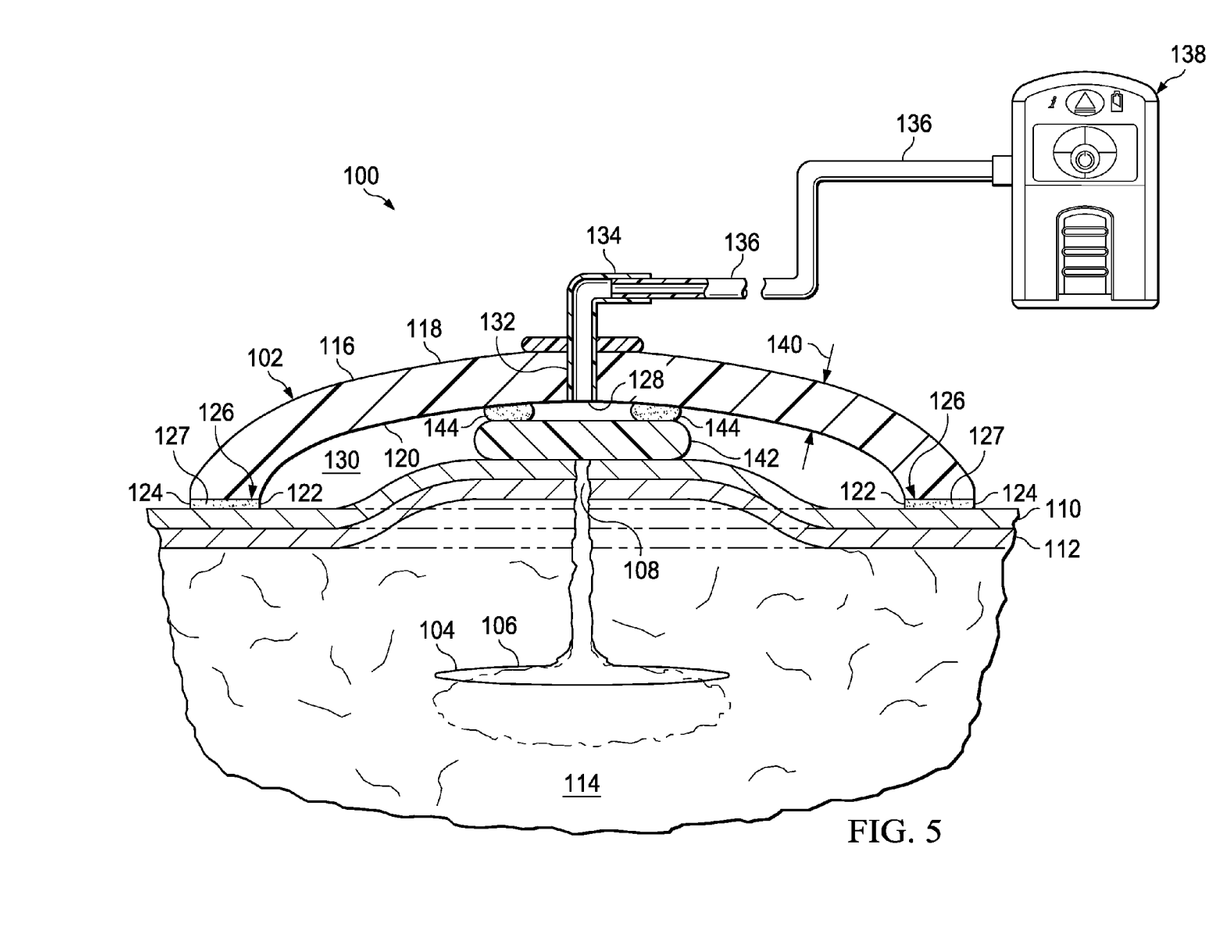
FIG. 5 is a schematic diagram with a portion in cross section of the illustrative, non-limiting system of FIG. 1 shown with reduced pressure applied.

This pulling of the epidermis 110 and associated tissue along with the delivery of reduced pressure to the surface wound 108 causes or helps the subcutaneous defect 104 to close or for portions to approximate each other as shown in FIG. 5. This in turn restores fully or partially the lymphatic flow that was disrupted by the subcutaneous defect 104 and this in turn helps fluids to be removed by the patient's body. The subcutaneous defect 104, before reduced pressure is applied, is shown in FIG. 1 and in FIG. 5 with broken lines. The application of the tissue-approximating system 100 may also help with profusion. Some fluids may be removed through the surface wound 108 as reduced pressure is applied.

In one illustrative, non-limiting embodiment, the curved member 116 is formed of a size and material to withstand the forces that develop under reduced pressure in the range of −100 to −200 mm Hg, but other ranges are possible. The forces developed in the curved member 116 are carried tangentially. As the reduced pressure increases, the epidermis 110 may be pulled so far into the concave space 130 that but for the spacer member 142, the reduced-pressure aperture 132 would close.

Figure 6:
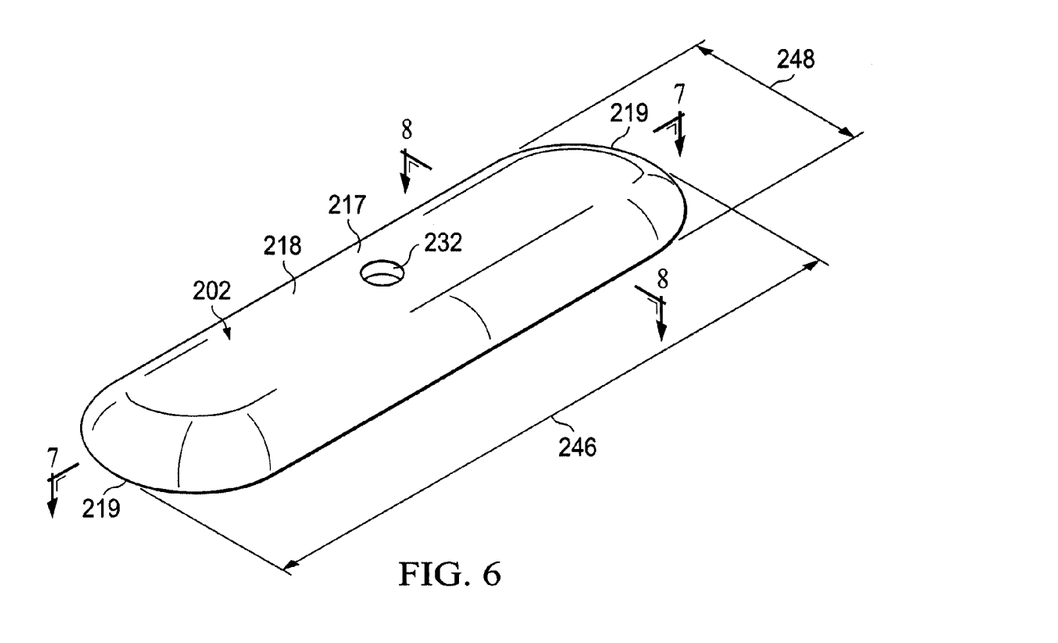
FIG. 6 is a schematic, perspective view of another illustrative, non-limiting embodiment of a curved member.
Figure 7:
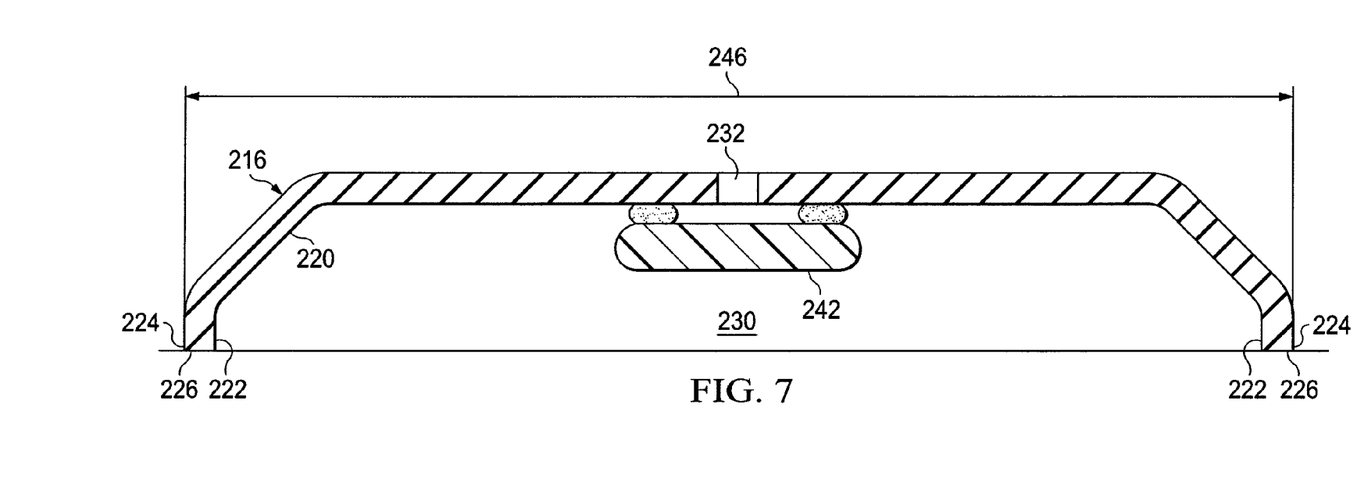
FIG. 7 is a longitudinal cross section of the curved member of FIG. 6.
Figure 8:
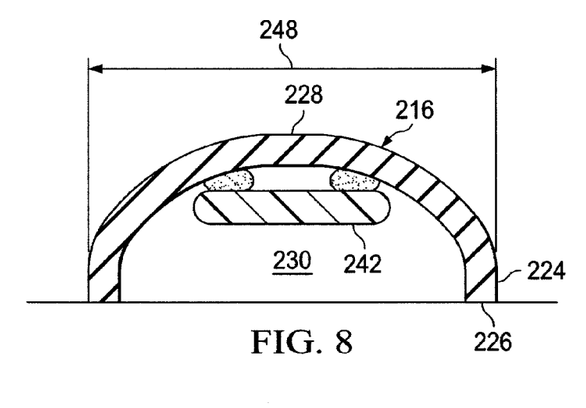
FIG. 8 is a lateral cross section of the curved member of FIGS. 6-7.

Referring now primarily to FIGS. 6-8, an illustrative, non-limiting embodiment of a tissue-approximating device 202 is presented. The tissue-approximating device 202 may be used with a tissue-approximating system, such as the tissue-approximating system 100 of FIGS. 1-5, and is particularly well suited for use with a linear surface wound, such as an incision. The tissue-approximating device 202 is analogous in many respects to the tissue-approximating device 102 of FIGS. 1-5 and analogous parts have been indicated by indexing them by 100.

The tissue-approximating device 202 has a curved member 216 with a first side 218 and a second, tissue-facing side 220. The curved member 216 may be formed with an inner perimeter 222 and an outer perimeter 224 that define a flange portion 226. The curved member 216 has an apex 228, which in the lateral cross section of FIG. 8 is the most vertical (for the orientation shown) portion. The apex 228 is displaced from the flange portion 226 in two dimensions. A portion of the curved member 216 defines a concave space 230 inboard of the inner perimeter 222 that includes the apex 228 on the second, tissue-facing side 220 of the curved member 216. A hydrogel or hydrocolloid may be added to the flange portion 226 to help seal the curved member 216 against the patient's epidermis to provide a fluid seal. The curved member 216 may formed with a longitudinal, concave body 217 and two end caps 219.

A reduced-pressure aperture 232 may formed on the curved member 216 and in this illustrative embodiment is located at the apex 228, but could be any where. The reduced-pressure aperture 232 facilitates fluidly coupling a reduced-pressure interface to the curved member 216 such that reduced pressure may be delivered to the concave space 230. A spacer member 242, or spacer, may be disposed in the concave space 230 to keep the reduced-pressure aperture 232 open.

The tissue-approximating device 202 has a longitudinal dimension 246 and a lateral dimension 248. The tissue-approximating device 202 typically has an aspect ratio (longitudinal dimension/lateral dimension) in the range of 2 to 20 and more typically in the range of 4 to 7.

The use of the tissue-approximating device 202 is analogous to the use of the tissue-approximating device 102 of FIGS. 1-5. The tissue-approximating device 202 is, however, particularly well suited for linear, surface wounds. The aspect ratio of the tissue-approximating device 202 means that the linear surface wound may be covered with a tissue approximating device that requires less material than a circular embodiment.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment.

We claim:

1. A method for tissue approximation for a subcutaneous tissue defect which is associated with a surface wound, the method comprising the steps of:

deploying a tissue-approximating device over the subcutaneous tissue and the surface wound, wherein the tissue-approximating device comprises:

a curved member formed from a semi-rigid material and having a first side terminating at an outer perimeter, a tissue-facing side terminating at an inner perimeter, and wherein the tissue-facing side of the curved member defines a concave space extending from the inner perimeter to an apex, a reduced-pressure aperture extending through the curved member in fluid communication with the concave space for receiving reduced pressure from a source of reduced pressure, a flange portion formed by the thickness of the curved member between the inner perimeter and the outer perimeter, and configured to be disposed adjacent intact epidermis, an attachment device coupled to the tissue-facing side of the curved member proximate the reduced-pressure aperture, and a spacer member coupled to the attachment device to form a breathable space between the apex, attachment device, and spacer member, the spacer member having a plurality of flow channels in fluid communication with the reduced-pressure aperture to distribute reduced pressure to the concave space;

fluidly coupling a reduced-pressure source to the concave space; and causing the reduced-pressure source to deliver reduced pressure to the concave space whereby portions of the subcutaneous tissue are approximated.

2. The method of claim 1, wherein the reduced-pressure aperture is formed at the apex.

3. The method of claim 1, wherein the curved member comprises a dome-shaped member.

4. The method of claim 1, wherein the spacer member comprises a foam.

5. The method of claim 1, wherein the spacer member comprises a non-woven material.

6. The method of claim 1, wherein the semi-rigid material is a medical-grade polymer and a curvature of the curved member provides for a tangential force when under compression.

7. The method of claim 1, wherein the semi-rigid material is a silicone and a curvature of the curved member provides for a tangential force when under compression.

8. The method of claim 1, wherein the step of causing the reduced-pressure source to deliver reduced pressure to the concave space comprises causing reduced pressure in the range of −90 to −220 mm Hg to be delivered to the concave space.

9. The method of claim 1, wherein the step of causing the reduced-pressure source to deliver reduced pressure to the concave space comprises causing reduced pressure in the range of −90 to −220 mm Hg to be delivered to the concave space with a variable pattern.

10. The method of claim 1, wherein the step of fluidly coupling a reduced-pressure source to the concave space comprises the steps of coupling a reduced-pressure interface to the reduced-pressure aperture and using a reduced-pressure conduit to fluidly couple the reduced-pressure interface to the reduced-pressure source.

11. The method of claim 1, wherein:
the reduced-pressure aperture is formed proximate the apex;
wherein the spacer member comprises a foam;
the step of causing the reduced-pressure source to deliver reduced pressure to the concave space comprises causing reduced pressure in the range of −90 to −220 mm Hg to be delivered to the concave space with a variable pattern;
the curved member and flange portion are formed of a semi-rigid, medical-grade polymer and the curvature of the curved member provides for a tangential force when under compression; and
the step of fluidly coupling a reduced-pressure source to the concave space comprises the steps of coupling a reduced-pressure interface to the reduced-pressure aperture and using a reduced-pressure conduit to fluidly couple the reduced-pressure interface to the reduced-pressure source.

12. The method of claim 1, wherein the surface wound is a linear wound and the curved member comprises a member having an aspect ratio of at least 4.

13. The method of claim 1, wherein the curved member has a thickness between one-sixth and one-twelfth of the diameter of the inner perimeter.

14. The method of claim 1, wherein the spacer member is positioned within the concave space above a plane defined by the inner perimeter.

15. A tissue-approximating device for approximating a subcutaneous tissue defect opening to a surface wound, the tissue-approximating device comprising:
a curved member formed from a semi-rigid material and having a first side terminating at an outer perimeter and a tissue-facing side terminating at an inner perimeter, and wherein the tissue-facing side of the curved member defines a concave space extending from the inner perimeter to an apex;
a reduced-pressure aperture extending through the curved member in fluid communication with the concave space for receiving reduced pressure from a source of reduced pressure;
a flange portion formed by the thickness of the curved member between the inner perimeter and the outer perimeter, and configured to be disposed adjacent intact epidermis;
an attachment device coupled to the tissue-facing side of the curved member proximate the reduced-pressure aperture; and
a spacer member coupled to the attachment device to form a breathable space between the apex, attachment device, and spacer member, the spacer member having a plurality of flow channels in fluid communication with the reduced-pressure aperture to distribute reduced pressure to the concave space;
wherein the curved member is shaped to transmit a tangential force of the curved member to the flange portion when reduced pressure is applied to the concave space.

16. The tissue-approximating device of claim 15, wherein the reduced-pressure aperture is formed at the apex.

17. The tissue-approximating device of claim 15, wherein the curved member comprises a dome shaped member.

18. The tissue-approximating device of claim 15, wherein the spacer member comprises a foam.

19. The tissue-approximating device of claim 15, wherein the spacer member comprises a non-woven material.

20. The tissue-approximating device of claim 15, wherein the semi-rigid material is a medical-grade polymer.

21. The tissue-approximating device of claim 15, wherein the semi-rigid material is a silicone.

22. The tissue-approximating device of claim 15, wherein the curved member has a thickness between one-sixth and one-twelfth of the diameter of the inner perimeter.

23. The tissue-approximating device of claim 15, wherein the spacer member is positioned within the concave space above a plane defined by the inner perimeter.

24. A method of manufacturing a tissue-approximating device for a subcutaneous tissue defect opening to a surface wound, wherein the method comprises:
forming a curved member from a semi-rigid material and having a first side terminating at an outer perimeter, a tissue-facing side terminating at an inner perimeter, and wherein the tissue-facing side of the curved member defines a concave space extending from the inner perimeter to an apex, and a flange portion formed by a thickness of the curved member between the inner perimeter and the outer perimeter, and configured to be disposed adjacent intact epidermis;
forming a reduced-pressure aperture extending through the curved member in fluid communication with the concave space for receiving reduced pressure from a source of reduced pressure;
coupling an attachment device coupled to the tissue-facing side of the curved member proximate the reduced-pressure aperture, and coupling a spacer member to the attachment device to form a breathable space between the apex, attachment device, and spacer member, the spacer member having a plurality of flow channels in fluid communication with the reduced-pressure aperture to distribute reduced pressure to the concave space.

25. The method of claim 24, wherein the step of forming a reduced-pressure aperture comprises forming the reduced-pressure aperture at the apex.

26. The method of claim 24, wherein the step of forming a curved member comprises forming a dome-shaped member.

27. The method of claim 24, wherein the step of providing a spacer member comprises the step of providing a foam member.

28. The method of claim 24, wherein the step of providing a spacer member comprises the step of providing a non-woven member.

29. The method of claim 24, wherein the semi-rigid material is a medical-grade polymer and a curvature of the curved member provides for a tangential force when under compression.

30. The method of claim 24, wherein the semi-rigid material is a silicone and a curvature of the curved member provides for a tangential force when under compression.

31. The method of claim 24, wherein the curved member has a thickness between one-sixth and one-twelfth of the diameter of the inner perimeter.

32. The method of claim 24, wherein the spacer member is positioned within the concave space above a plane defined by the inner perimeter.

\* \* \* \* \*